(12) United States Patent
Tsai et al.

(10) Patent No.: US 10,745,723 B2
(45) Date of Patent: Aug. 18, 2020

(54) METHOD FOR INCREASING PHAS CONTENT OF WASTE SLUDGE BY FERMENTING THE WASTE SLUDGE TO PRODUCE VOLATILE FATTY ACID

(71) Applicant: NATIONAL CHI NAN UNIVERSITY, Nantou County (TW)

(72) Inventors: Yung-Pin Tsai, Nantou County (TW); Meng-Shan Lu, Nantou County (TW); Chih-Chi Yang, Nantou County (TW); Hao Shiu, Nantou County (TW); Jan-Wei Lin, Nantou County (TW); Yu-Wei Liou, Nantou County (TW)

(73) Assignee: National Chi Nan University, Nantou County (TW)

( * ) Notice: Subject to any disclaimer, the term of this patent is extended or adjusted under 35 U.S.C. 154(b) by 94 days.

(21) Appl. No.: 15/866,285

(22) Filed: Jan. 9, 2018

(65) Prior Publication Data

US 2019/0177753 A1 Jun. 13, 2019

(30) Foreign Application Priority Data

Dec. 7, 2017 (TW) .............................. 106142979 A (51) Int. Cl.
```
C02F 11/02      (2006.01)
C12N 1/36       (2006.01)
C12P 7/62       (2006.01)
C12P 7/64       (2006.01)
C02F 11/04      (2006.01)
C02F 103/36     (2006.01)
C02F 1/66       (2006.01)
```

(52) U.S. Cl.
CPC .............. *C12P 7/625* (2013.01); *C02F 11/02* (2013.01); *C02F 11/04* (2013.01); *C12N 1/36* (2013.01); *C12P 7/6409* (2013.01); *C02F 1/66* (2013.01); *C02F 2103/365* (2013.01)

(58) Field of Classification Search
None
See application file for complete search history.

(56) References Cited

U.S. PATENT DOCUMENTS

| | | | | |
|---|---|---|---|---|
| 2012/0301933 | A1* | 11/2012 | Smith | ...................... C12P 7/625 435/135 |
| 2013/0029388 | A1* | 1/2013 | Werker | ...................... C02F 3/30 435/135 |
| 2013/0122559 | A1* | 5/2013 | Lan | .......................... C12P 7/625 435/135 |

FOREIGN PATENT DOCUMENTS

CN    101314783    * 12/2008

* cited by examiner

*Primary Examiner* — Blaine Lankford
*Assistant Examiner* — Lauren K Van Buren
(74) *Attorney, Agent, or Firm* — Muncy, Geissler, Olds & Lowe, P.C.

(57) ABSTRACT

The present invention relates to a method for increasing polyhydroxyalkanoates (PHAs) content of waste sludge, by taking the fermentation liquid fermented from waste sludge as a carbon source, and performing ADF domestication process, thereby quickly raising PHAs contentin the waste sludge, in accordance with the method of the present invention, the conventional complicated domestication steps is simplified and a higher content PHAs can be produced, additionally the added carbon source of the present invention is the VFA fermented by the waste sludge, so it's unnecessary to add extra material, therefore including more industrial utilization.

6 Claims, 8 Drawing Sheets

PHAs production Comparasion between the method of the invention and other documents

| Producing way | Temp (°C) | Ph | Carbon source | PHA | Best time | Production | From |
|---|---|---|---|---|---|---|---|
| Life waste sludge Anaerobic-aerobic (not domesticated) | 18-25 | 8 | Life wastewater+ Acetic acid | HB | NA | 30% | Chua(2003) |
| Life waste sludge ADF (not domesticated) | 21 | 8.1-8.6 | VFA | HB:HV(88.1:11.9) | 220min | 56.50% | Mengmeng(2009) |
| Life waste sludge ADF (domesticated) | 25 | 8.88-9.04 | Butyric acid | HB 100% | 462min | 0.280 g COD/Gcod | Chen(2008) |
| Life waste sludge ADF (domesticated) | 25 | 9.01-9.14 | Propionic acid | HB:HV(26.2:73.8) | 462min | 0.311 g COD/Gcod | Chen(2008) |
| Life waste sludge ADF (domesticated) | 25 | 9.13-9.15 | Acetic acid | HB 100% | 462min | 0.700 g COD/Gcod | Chen(2008) |
| GAO germ | 30 | 7.7 | Molasses(35 Cmmol/L) | HB:HV:HHx(56:43:1) | 120min | 37% | Lemos(2010) |
| Life waste sludge ADF (domesticated) | 25 | 9.5 | Mixture of Acetic acid and Propionic acid | HB:HV(80:20) | 510min | 46% | Majone(2010) |
| Life waste sludge ADF (domesticated) | 30 | 7.3 | Wastewater of paper mill | HB:HV(39:61) | 1440min | 48% | Bengtsson(2008) |
| Life waste sludge ADF (domesticated) | 28-30 | 7 | Wastewater of Fermented palm oil plant | HB:HV(77:23) | 480min | 64% | Chua(2015) |
| Life waste sludge ADF (domesticated) | NA | NA | Wastewater of paper mill | NA | NA | 67% | Serafim(2014) |
| Mixed microbial culture | 23-25 | 8.4 | VFA(497 Cmmol/L) | HB:HV(61:39) | 360min | 72% | Reos(2011) |
| Life waste sludge ADF (domesticated) | 22 | NA | Acetic acid(180 Cmmol/L) | HB | 200min | 78.50% | Serafim(2004) |
| Mixed microbial culture(domesticated) | 30 | 7 | Acetic acid | HB 100% | NA | 84% | Kleerebezem(2010) |
| Waste sludge in fermentation industry concentration tank | 25 | 7.5 | VFA(400 mg/L) | HB:HV(37.5:62.5) | 1193min | 70.40% | The present study |

FIG. 8

METHOD FOR INCREASING PHAS CONTENT OF WASTE SLUDGE BY FERMENTING THE WASTE SLUDGE TO PRODUCE VOLATILE FATTY ACID

FIELD OF THE INVENTION

The present invention relates to a method for increasing polyhydroxyalkanoates (PHAs) content of waste sludge, in particular, taking the fermentation liquid fermented from waste sludge as a carbon source, and injecting the fermentation liquid into the waste sludge aerated and activated by Oxygen to domesticate microorganisms, and the saturated dissolved oxygen of waste sludge can be a basis to judge whether the carbon source is exhausted, therefore raising the productivity and content of the polyhydroxyalkanoates (PHAs) in the cell.

BACKGROUND OF THE INVENTION

Since 1960 decade, the Petrochemical industry of Taiwan has been growing along with the construction quantity of Petrochemical industry, and the development of Petrochemical industry has been also gradually improved. Broadly speaking, the Petrochemical industry regards a final product processed from Petrochemical raw materials manufactured by oil or nature gas.

The relative field of the Petrochemical industry includes: Basic chemical materials manufacturing; Petrochemicals Manufacturing; Fertilizers Manufacturing; Synthetic Resin, Plastic Materials Manufacturing; Synthetic rubber and Man-made Fibers Manufacturing. Petrochemicals can include Ethylene, Propylene, Butadiene, benzene, toluene and Xylene, etc. The aforesaid raw materials can be transformed to intermedia materials via processes such as high-temperature and high-pressure Pyrolysis, and a verity of plastics, rubber, Synthetic Fibers and chemicals can be achieved by chemical processes including polymerization, esterification or alkylation, and a final product can be achieved by processing aforesaid polymaterials via specific processes. Therefore, Petrochemical products are everywhere in daily life so as to be inseparable with the modern livelihood needs.

Although Petrochemical products bring convenience for our life, the synthetic polymer materials so called synthetic plastic such as Polypropylene, Polyethylene, PVC and Polystyrene have extremely high chemical stability, high acid and alkali-resistance and are free of mold and erosion. The synthetic plastic is the main ingredient of city solid waste and is even called white population. To slow down the environmental damage resulted from synthetic plastic, partial nations have published relative acts to restrict the usage of traditional plastic bags and promoted people to use own green bags. In addition to lowering the usage of traditional plastic bags, each country also put into the development of the alternative materials of traditional plastic bags or replace the traditional plastic bags with Biodegradable Plastic (BDP).

Biodegradable Plastic, or called biodegradable plastic well known by people can be also called green plastic. In a natural landfill or composting environment, a green plastic can be metabolized and decomposed by microorganisms to generate water, Carbon dioxide or Methane, therefore the green plastic is a plastic material capable of being degraded in natural and is less harmful to the environment. Among various plastic materials capable of decomposed in biological, the BDP is considered to be one having more prospect because of capable of being completely degraded in biological, wherein Polyhydroxyalkanoate (PHAs) can be further applied to Biomedical materials, Tissue engineering materials, Electrical materials and Packaging materials because of including features of biodegradable and biocompatibility.

The thermoplastic of PHAs is similar to that of the Petrochemical plastic (Lee, 2012). PHAs are intracellular polyesters intracellularly synthesized by various sorts of bacterial. Currently, most of the relative researches of PHAs are performing pure culture by using species capable of accumulating PHAs to investigate a best condition for producing PHAs. By using pure culture, PHAs can be produced more, however, the operation cost may correspondingly raise when PHAs is produced under the best condition. In another aspect, the sewage treatment proportion have been much raised corresponding to the rapidly growing quantities of sewage treatment plant. Further, outsourcing treatment is urgently needed by lots of waste sludge produced every year. The cost of treating waste sludge has been raised day by day so as to occupy 60% of the total cost of a sewage treatment plant (Wei et al, 2003), and the sewage treatment industries are difficult to deal with the problem.

Concluding theparts to be improved of current technology and the problems to be solved in the industry, the present invention provides a concept that producing PHAs by reusing waste sludge, at the same time the objects including lowering the cost of producing PHAs, simplifying the produce of PHAs, speeding the productivity of PHAs and treating excess waste sludge can be achieved, therefore promoting the industrial utilization of PHAs.

SUMMARY OF THE INVENTION

Based on aforesaid reasons, the present invention provides a method for increasing PHAs content of waste sludge. The method includes fermenting waste sludge in a proper condition to get a fermentation liquid having higher proportion of volatile fatty acid content, therefore the waste sludge can be a good carbon source for domesticating microorganisms.

In another aspect, the method includes diluting waste sludge with water, processing aeration and activation by using Oxygen and injecting aforesaid fermentation liquid to the activated waste sludge to domesticate microorganisms, therefore effectively reusing waste sludge to solving the problem of increasingly waste sludge.

In another aspect, the method includes injecting the fermentation liquid to the activated waste sludge to when the saturated dissolved oxygen thereof reaches 75%~85%, and reinjecting the fermentation liquid to the activated waste sludge when the saturated dissolved oxygen thereof drops to 65%~75%. Accordingly the consumption of carbon source can be effectively monitored via a simple flow, and the Food to Microorganism (F/M) can be also effectively adjusted, therefore the productivity and accumulation rate of PHAs can be largely raised.

To achieve above objects, the present invention provides a method for increasing PHAs content of waste sludge, including steps of: (1) diluting the waste sludge with water and performing Oxygen aeration and activation to get an activated waste sludge; (2) fermenting another waste sludge other than the activated and aerated waste sludge for 4~6 days at a temperature of 40° C.~50° C. to get a fermentation liquid; and (3) injecting the fermentation liquid into the activated waste sludge to perform microorganism domestication and synthesize PHAs; wherein when the Dissolved Oxygen (DO) of the activated waste sludge reaches 75%~85%, injecting the fermentation liquid to the activated waste sludge to synthesize PHAs and reinjecting the fermentation liquid to the activated waste sludge when the DO of the activated waste sludge drops to 65%~75%, and repeating the steps for 5~10 times.

In an embodiment, before the step of diluting the waste sludge, the waste sludge is filtered to remove Impurities and the PH value thereof is adjusted to 11.

In an embodiment, in the step of diluting the waste sludge, the ratio of mixing the waste sludge and water is 1:1.

In an embodiment, in the step of fermenting, the waste sludge is fermented with 40° C. for 5 days.

In an embodiment, in the step of synthesizing PHAs, the fermentation liquid including volatile fatty acid having 300~500 mg/L concentration is added to the waste sludge to perform synthesizing.

In an embodiment, the volatile fatty acid is selected one of the group consisting of: Acetic acid (HAc), Propanoic acid (HPr), Isobutyric acid (iso-HBu) and Valeric acid (HVa), or any combination thereof.

In an embodiment, when the Dissolved Oxygen (DO) of the activated waste sludge reaches 80%, injecting the fermentation liquid to the activated waste sludge to synthesize PHAs and reinjecting the fermentation liquid to the activated waste sludge when the DO of the activated waste sludge drops to 70%, and repeating the steps for 8~10 times.

In addition, the present invention provides a fermentation liquid of waste sludge for producing PHAs in waste sludge, the waste sludge is a raw material to be directly fermented by the fermentation liquid and can be a carbon source to perform microorganism domestication and produce PHAs, therefore the waste sludge can be reused to lower the process cost of a sewage treatment plant and the amount of waste sludge can be effectively decreased.

To achieve above objects, the fermentation liquid of waste sludge for producing PHAs in waste sludge includes volatile fatty acid having 1200~1500 mg/L concentration and produced by following steps of: (1) filtering a waste sludge to remove impurities and condense the waste sludge; (2) Evenly mixing the waste sludge and adjusting the PH value thereof to 10.5~11.5; and (3) fermenting the waste sludge with 40° C. for 4-6 days to achieve the fermentation liquid of waste sludge.

In an embodiment, the volatile fatty acid is selected one of the group consisting of: Acetic acid (HAc), Propanoic acid (HPr), Isobutyric acid (iso-HBu) and Valeric acid (HVa), or any combination thereof.

In an embodiment, in the step of fermenting, the PH value of the waste sludge is 11 and the waste sludge is fermented with 40° C. for 5 days.

BRIEF DESCRIPTION OF THE DRAWINGS

FIG. 8 illustrates a comparison of PHAs production of the present invention and that of other documents.

DETAILED DESCRIPTION OF THE INVENTION

Other features and advantages of the present invention will be described in advance in following embodiments, and the following embodiments are used to help the illustration of the drawings instead of restricting the scope of the present invention.

Polyhydroxyalkanoates (PHAs) belongs to a sort of biodegradable raw material and can be widely applied because of the biodegradable and compatibility thereof. However, the producing cost of PHAs remains expensive, and the producing flow thereof is complicated and the problem regarding accumulation and processing cost of waste sludge grows year by year. In accordance with above problems, the present invention provides a method for increasing PHAs content of waste sludge by fermenting the waste sludge to produce volatile fatty acid for expecting to solve the issue of above current technologies. The following description is directed to the technical means and features.

Figure 1:
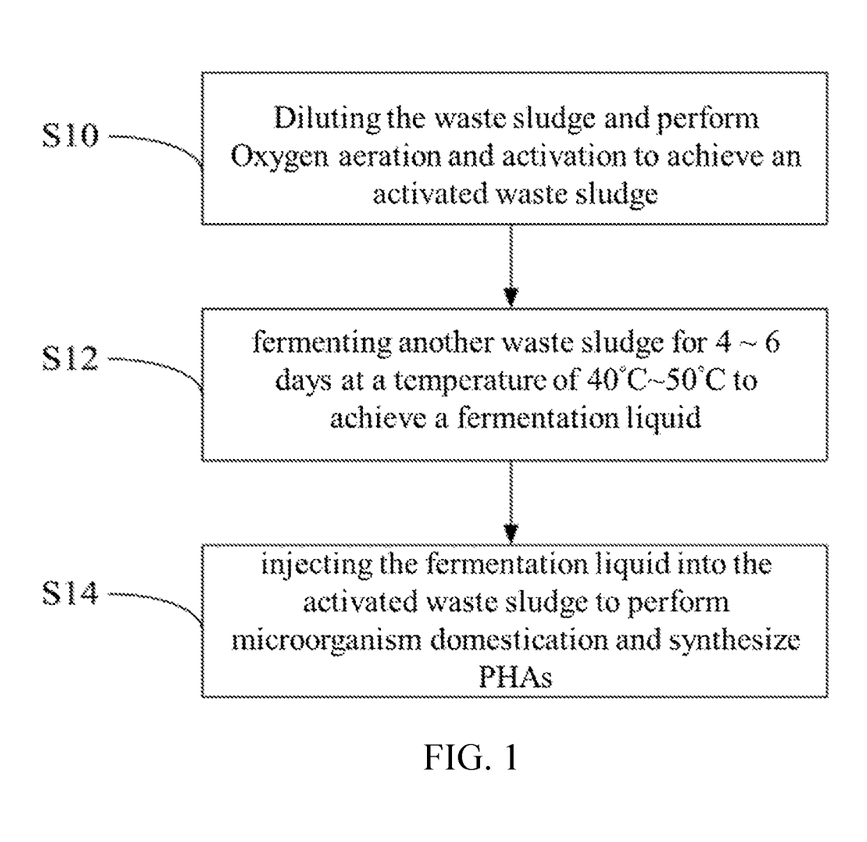
FIG. 1 is a schematic flow diagram of a first embodiment of the present invention.

Please refer to FIG. 1, a schematic flow diagram of a first embodiment of the present invention is disclosed. As shown in the drawing, the method for increasing PHAs content of waste sludge includes steps of:

Step S10: diluting the waste sludge with water and performing Oxygen aeration and activation to get an activated waste sludge;

Step S12: fermenting another waste sludge other than the activated and aerated waste sludge for 4~6 days at a temperature of 40° C.–50° C. to get a fermentation liquid;

Step S14: injecting the fermentation liquid into the activated waste sludge to perform microorganism domestication and synthesize PHAs.

Figure 2:
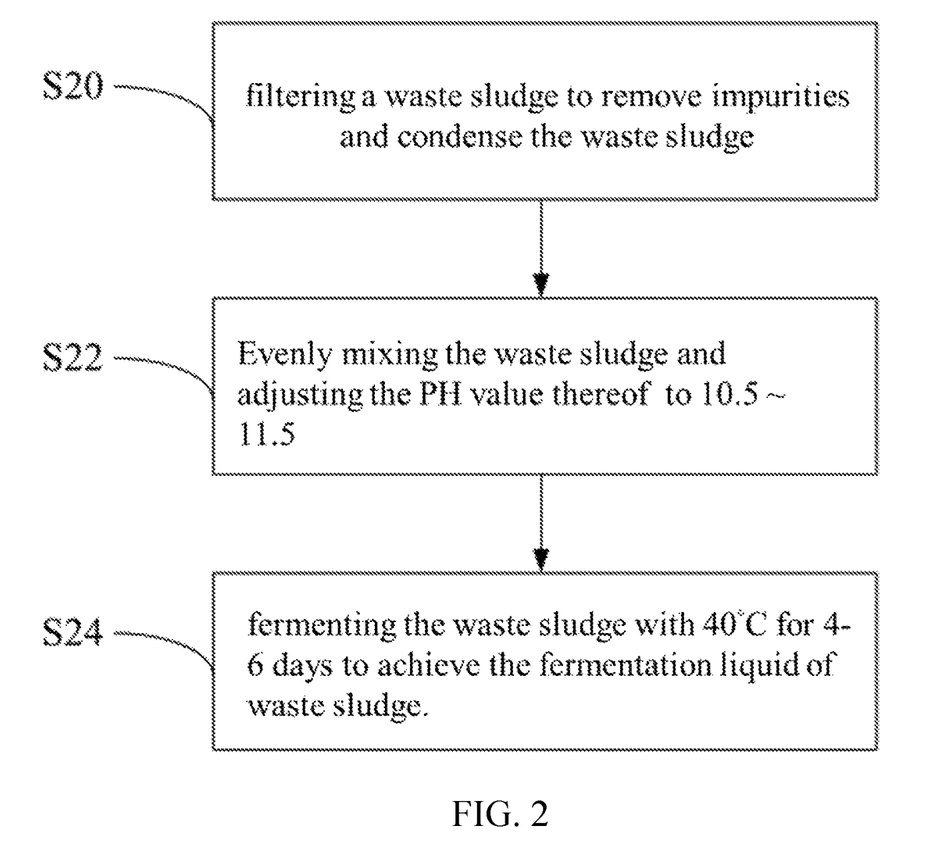
FIG. 2 is a schematic flow diagram of a second embodiment of the present invention.

Before the Step 10, as the steps S20 and S22 shown in FIG. 2, the waste sludge has been performed first, further, the waste sludge is filtered to remove large size impurities such as stones or leaves, and the PH value of the processed waste sludge is adjusted to 10.5 to 11.5. In a preferred embodiment, the PH value of the processed waste sludge is adjusted to 11 and is set aside with 40° C. for at least 12 hours for condensing the waste sludge to be backup.

The aforesaid waste sludge can be taken from any type one such as daily-life waste sludge, hospital waste sludge, fermentation industry waste sludge or animal husbandry. In the present embodiment, a fermentation industry waste sludge in the concentrate tank is selected to be a source waste sludge. The waste sludge in the concentrate tank is from primary sludge and final sludge, and the volume ratio between the primary sludge and final sludge is about 1:3 (v/v). In addition, before being proceed, the fundamental feature of the waste sludge in the concentrate tank is shown as next table:

TABLE 1

FUNDAMENTAL FEATURE OF THE WASTE SLUDGE

| Appellation | Original waste sludge |
|---|---|
| SS | 15,210~18,360 (mg/L) |
| VSS | 12,980~15,610 (mg/L) |
| TCOD | 22,110~22,319 (mg/L) |
| SCOD | 144~172 (mg/L) |
| DOC | 20.5~27.9 (mg/L) |
| $NH_4^+$—N | 64.1~78.8 (mg/L) |
| $TPO_4$—P | 2.47~2.97 (mg/L) |
| VFA | 0.00 (mg C/g VCC) |

TABLE 2

EACH TYPE OF VFA CONTENT OF THE FERMENTATION LIQUID

| ITEM | CONCENTRATION (mg/L) |
|---|---|
| Acetic acid | 415 |
| Propionic acid | 350 |
| Isobutyric acid | 98 |
| Butyric acid | 214 |
| Valeric acid | 285 |
| Total VFA | 1,335 |

The Step S10 is for fully aerating the waste sludge with Oxygen to activate the waste sludge, thereby providing the needed Oxygen to the aerobic microbiota in the waste sludge for next domestication. For achieving a better aeration and activation effect, the waste sludge in the embodiment is diluted with a proper solvent, and in a preferred embodiment, RO water and the waste sludge is mixed with 1:1 to dilute the waste sludge, therefore after aerating the diluted waste sludge to Oxygen, Oxygen can be evenly spread in the waste sludge for achieving a better activation effect.

In another aspect, PHAs can be an accumulation material for saving carbon source, energy or reducing power in most microorganism cells. With an outside carbon source, many microorganisms can ingest matrix (outside carbon source) to synthesize PHAs even lacking the basic element (ex. N, P, S, O and Mg) for growing (Lee and Chang, 1994, Ander and Dawes, 1990, Roy et al., 2015). After ingesting different sorts of carbon sources, in addition to the metabolic pathways of cells are different, the synthesized PHAs are different, too. Furthermore, the PHAs capable of being synthesized by microorganisms is primary combined by polyhydroxybutyrate (PHB) and Polyhydroxybutyrate-valerate (PHV), and both of them have better Bio-compatibility and BIO-degradability in comparison with other PHAs. The combining percentage of PHB and PHV can be determined by the provided matrix type and the extent of hydrolysis, that is, if the matrix type is simple and the extent of hydrolysis is high, the acetic acid content is high, and the combining percentage of synthesized PHB is correspondingly high. Accordingly, the sort of carbon source may need to be considered for controlling the type of PHAs produced by microorganisms.

For effectively using the waste sludge and lowering the raw material cost of producing PHAs at the same time, in the Step S12 of the present embodiment, another set of processed waste sludge is taken to perform fermentation to directly get the carbon source from the waste sludge for feeding the microorganisms in following steps. In the present embodiment, the waste sludge is set aside with 40°~50° C. for 4~6 days fermentation, and in a preferred embodiment, it is set aside with 40 C for 5 days.

The achieved fermentation liquid via aforesaid fermentation reaction includes Volite Fatty Acid (VFA) with 1,200~1,500 mg/L concentration range, and the volatile fatty acid is selected one of the group consisting of: Acetic acid (HAc), Propanoic acid (HPr), Isobutyric acid (iso-HBu) and Valeric acid (HVa), or any combination thereof. In an embodiment, each type of VFA content of the fermentation liquid achieved by the fermentation reaction in Step S12 can be shown as table 2, wherein Acetic acid and Propionic acid have higher content than that of other VFA, and the contents of Acetic acid and Propionic acid are 31% and 26%, respectively.

Continually, after achieving the fermentation liquid having much VFA, as the description of Step S14, injecting the fermentation liquid of S12 into the activated sludge of Step S10 to perform microorganism domestication to promote synthesizing cells and accumulating PHAs.

Fast and famine cycling (Salehizageh et al. 2004) is a method for domesticating microorganisms and capable of promoting a microorganism saving the carbon source in the cell thereof. In the present embodiment, aerobic dynamic feeding (ADF) is selected to achieve the Fast and famine cycling. In advance, in the present embodiment, the fermentation liquid is an outside carbon source capable of using and provided to the activated waste sludge in batches and continually. When the fermentation liquid is just injected into the activated waste sludge, it is a super-saturated status of the carbon source, and the cells may perform cell growth or save PHAs after ingesting carbon. When the injected outside carbon is exhausted, it is a super-hungry of the carbon source, and the PHAs saved by the cells is used to be the growth energy for cells (Lemos et al., 2004; Dionisi et al., 2005; Johnson et al., 2010; Majone et al., 1996; Loosdrecht and Heijnen, 2002; Dias et al., 2006), however, the rate of the PHAs accumulated in the cells is higher than the rate of cell growth, accordingly the PHAs can be accumulated in the cells (Serafim et al., 2004)

As mentioned above, in the duration of ADF, it is necessary to supplement the carbon source to make the sells return the super-saturated status, thereby raising the productivity and accumulation rate of PHAs in the microorganisms, and when the carbon source is injected into the tank with the activated waste sludge, the Dissolved Oxygen (DO) may decline in association with the Oxygen consumption of the microorganism, and when the carbon source is going to be exhausted, the DO will return to rise. Accordingly, in the present embodiment, when the waste sludge performs Oxygen aeration in Step S10, the DO of the achieved activated waste sludge is controlled to 75%~85% (6.18~7.01 mg/L, 25° C.), and after injecting the fermentation liquid into the activated waste sludge, monitoring the DO variation of the activated waste sludge at the same time, when the DO drops to 65%~75% (5.36~6.18 mg/L, 25° C.), re-adding the fermentation liquid and repeating 5~10 times. In a preferred embodiment, adding the fermentation liquid when the DO reaches 80% (6.6 mg/L, 25° C.), and when the DO drops to 70%, re-adding the fermentation liquid and repeating 8~10 times. By the mentioned method for domesticating microorganisms, the status of microorganism consuming outside carbon source can be monitored by an easier flow, therefore the outside carbon source can be re-added accurately and the Food to Microorganism (F/M) can be controlled to be 0.19±0.08, thereby achieving a high-efficiency Fast and famine cycling.

Other features and advantages of the present invention will be described in advance in following embodiments, and the following embodiments are used to help the illustration of the drawings instead of restricting the scope of the present invention.

In accordance with the production and ingredient of VFA achieved by the fermentation of the waste sludge may be different corresponding to the fermentation temperature and time, and the activation of the waste sludge also effects the microorganism domestication and the efficiency of synthesizing PHAs. Further, the culture condition and adding mode for the microorganism domestication also have much to do with the production and accumulation efficiency of PHAs. Accordingly, the present invention will discuss the parameter conditions of the preferred embodiments by the following examples.

Experimental Method

Analysis of the VFA Concentration

In the present invention, the VFA concentration of the solvent can be analyzed by a Gas-chromatography-mass spectrometry (GC-MS), and the analysis column is DB-FFAP, and the length of the column is 30 m, and the inner diameter of the column is 0.31 mm. The analysis conditions of the GC-MS: the temperature of the injection opening is 200° C., and the temperature of the detector opening is 250° C., and the temperature of the drying oven is 60° C., and the carrier gas is Helium (He, 99.995%), and the flow rate of the carrier gas is 46.8 mL/min, and the split ratio is 13:1, and the volume of the injected sample is 2 μl, and the analysis time is 14 minutes.

Analysis of the PHAs Concentration

In the present invention, the PHAs concentration of the solvent can be analyzed by a Gas-chromatography-mass spectrometry (GC-MS), and the analysis column is DB-1, and the length of the column is 30 m, and the inner diameter of the column is 0.25 mm. The analysis conditions of the GC-MS: the temperature of the injection opening is 220° C., and the temperature of the detector opening is 230° C., and the temperature of the drying oven is 70° C., and the carrier gas is Helium (He, 99.995%), and the flow rate of the carrier gas is 2.8 mL/min, and the split ratio is 15:1, and the volume of the injected sample is 2 μl, and the analysis time is 10 minutes.

Statistics Analysis

In the present invention, SPSS (PASW Statistics18) software is used for analysis, and the chosen analysis method is one way ANOVA and paired sample T test to confirm whether the production variation data of VFA caused by temperature is apparently different from that of PHAs domesticated by ADF with different conditions.

Figure 3A:
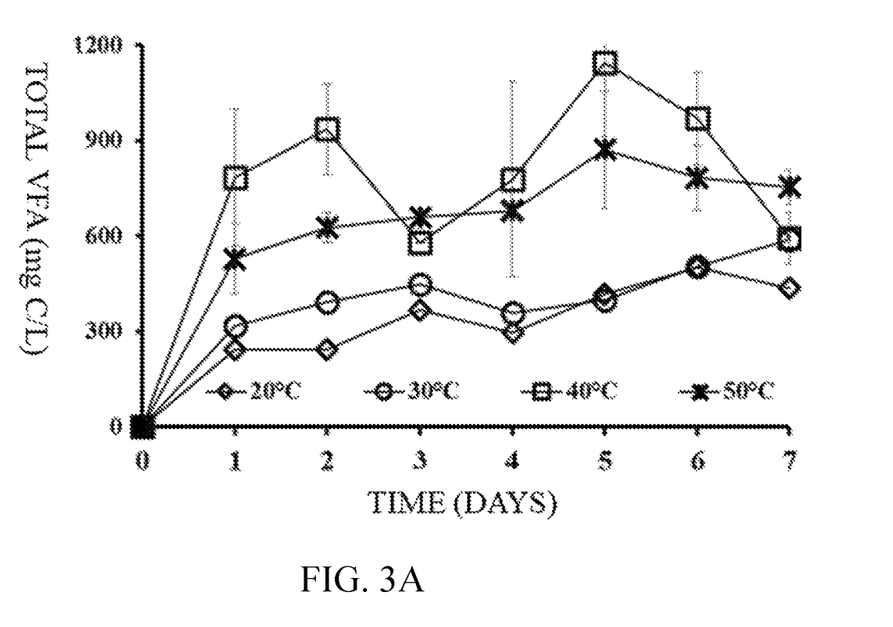
FIGS. 3A to 3B illustrate that the fermentation temperature and days influence the production of the volatile fatty acid and the total volatile fatty acid.
Figure 3B:
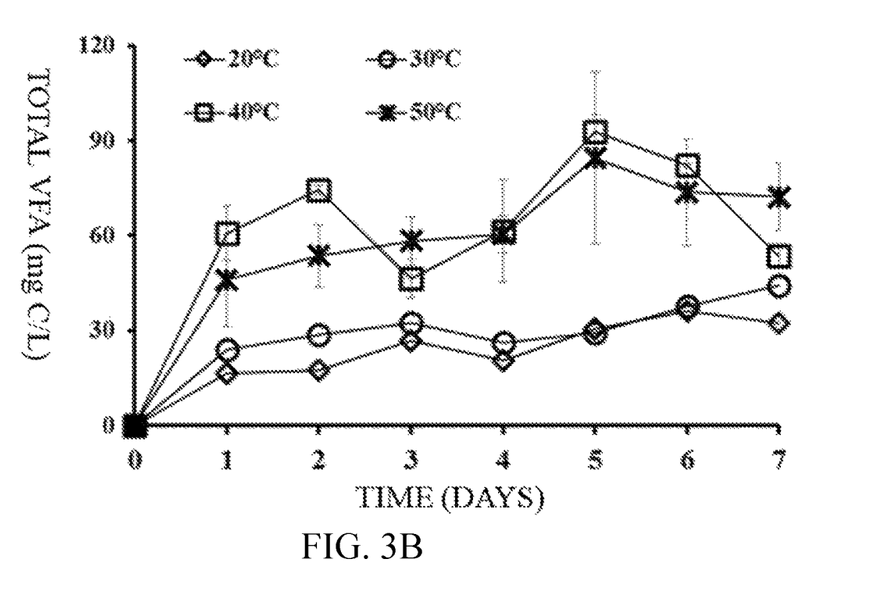

Embodiment 1 the Influence of the Fermentation Temperature and Days to VFA Total Production Please refer to FIGS. 3A and 3B, wherein FIG. 3A is a variation chart that different waste sludge, fermentation temperature and days correspond to the generated VFA concentration, and FIG. 3B is a VFA production variation chart that different waste sludge, fermentation temperature and days correspond to the microorganism. From the result, it can be realized that when the fermentation temperature is 40° C. and 50° C., the VFA production is higher than that of the fermentation temperature is 20° C. and 30° C. When the fermentation temperature is 40° C., the VFA concentration from the first fermentation day to $7^{th}$ day is 785, 935, 578, 779, 1144, 970 and 593 mg/L, respectively, as shown in FIG. 3A, and the VFA production of each unit microorganisms is 60.8, 74.3, 46.5, 61.5, 92.9, 82.1 and 53.5 mg (mg VFA/g VSS), respectively, as shown in FIG. 3B. So when the waste sludge is fermented with 40° C., the best fermentation days is 5 days. In addition, when the fermentation temperature is 50° C., the VFA concentration from the first fermentation day to $7^{th}$ day is 528, 627, 658, 679, 871, 783 and 754 mg/L, respectively, as shown in FIG. 3A, and the VFA production of each unit microorganisms is 46, 53.7, 58.4, 60.5, 84.5, 73.8 and 72.2 mg (mg VFA/g VSS), respectively, as shown in FIG. 3B. So when the waste sludge is fermented with 50° C., the best fermentation days is 5 days. In accordance with above result and the SPSS analysis software, when the fermentation temperatures of the waste sludge are 40° C. and 50° C., respectively, the produced VFA concentrations are not apparently different to each other. Accordingly, in a preferred embodiment of the present invention, the fermentation is performed with 40° C. for 5 days so as to effectively use the waste sludge and lower processing cost and energy consumption.

Embodiment 2 Activating the Waste Sludge

Figure 4A:
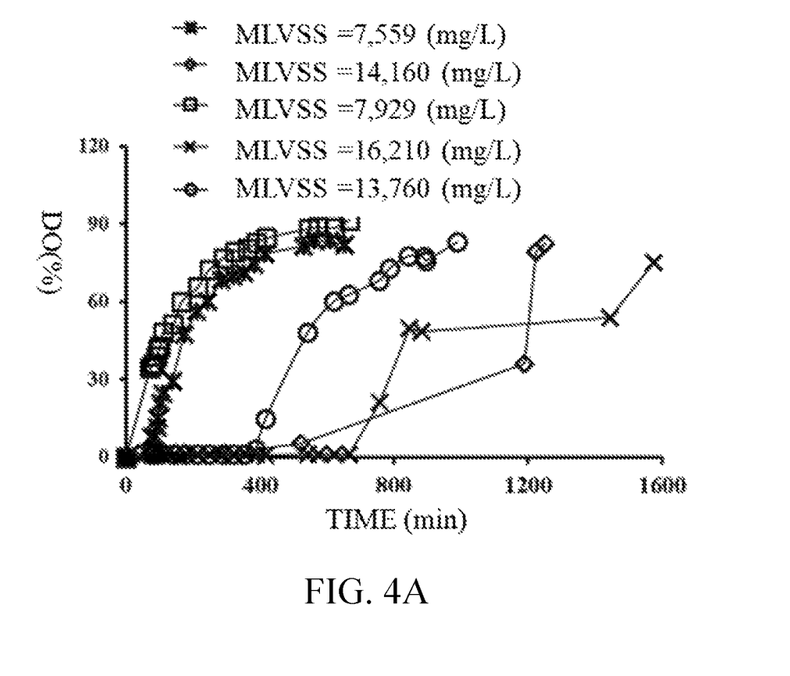
FIGS. 4A to 4B illustrate the activation of the waste sludge.
Figure 4B:
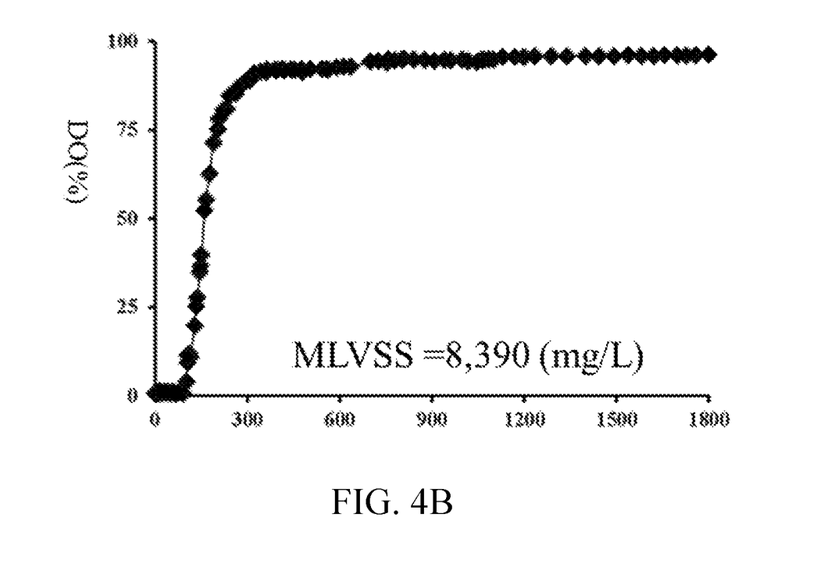

Please refer to FIGS. 4A and 4B, wherein FIG. 4A illustrates the activation phenomenon of different concentration, and FIG. 4B illustrates the activation phenomenon of a long time observation. In the result of FIG. 4A, for the group of mixed liquor volatile suspended solids (MLVSS) being 7,000±1,000 mg/L, the waste sludge is diluted with RO water by 1:1 ratio for performing the next experiment. As for the group of MLVSS being 15,000±1,500 mg/L, the waste sludge is an original waste sludge not diluted, wherein the diluted waste sludge can reach 80% DO fast after being aerated by Oxygen. As for the original sludge not diluted, it is obvious that the DO did not practically rise within 400 minutes after the waste sludge being aerated, and the spending time (989 minutes) for the DO reach 80% is practically 3 times of that of the diluted waste sludge. In addition, by considering a possibility that when the waste sludge reaches 80% DO in an aeration, the DO may false rise and then drop—the DO has not reached a balance, because a portion of the microorganisms consume the organic material in water but another portion of the microorganisms have not waken. Accordingly, the aeration time is extended for keeping observing the DO, and the result is shown in FIG. 4B, the diluted waste sludge remains a steady DO. Accordingly, in a preferred embodiment, the waste sludge is diluted with water before perform Oxygen activation.

Figure 5:
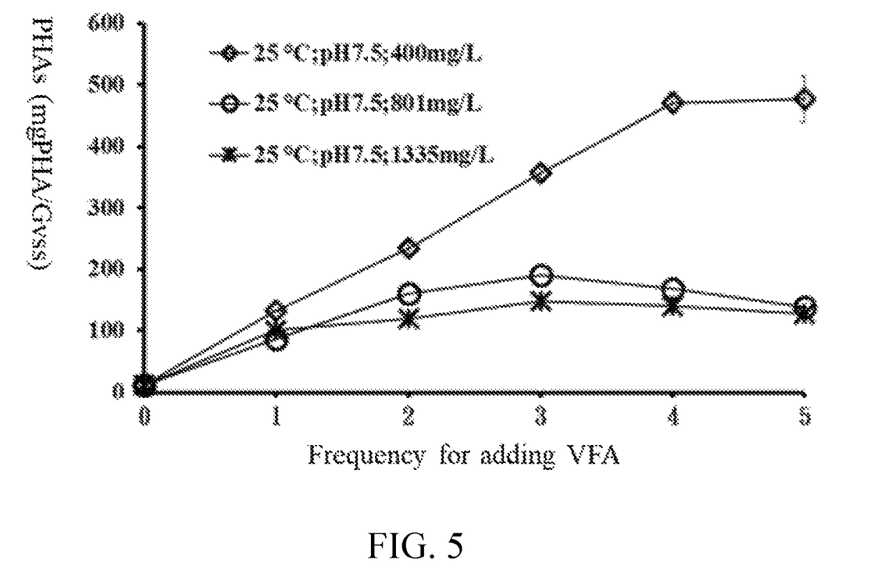
FIG. 5 illustrates a best concentration of volatile fatty acid for domesticating microorganism with Aerobic Dynamic Feeding (ADF).

Embodiment 3 the Best Adding VFA Concentration of ADF Domestication Microorganism Please refer to FIG. 5, which illustrates that different VFA concentrations influence the PHAs production after domesticating microorganism with Aerobic Dynamic Feeding (ADF). The experiment uses different VFA concentrations (400, 801, and 1,335 mg/L, respectively) to perform ADF domestication, as shown in the drawing, X axis is the process time of VFA, and Y axis is the production of PHAs (mg PHA/g VSS). As the result, when ADF domestication is performed and the VFA concentration is 400 mg/L, high PHAs production can be achieved in a short period, and the PHAs production is apparently higher than that when the VFA concentrations are 801 or 1,335 mg/L. Accordingly, in a preferred embodiment of the present invention, 400 mg/L VFA concentration is for performing ADF domestication microorganism.

Figure 6A:
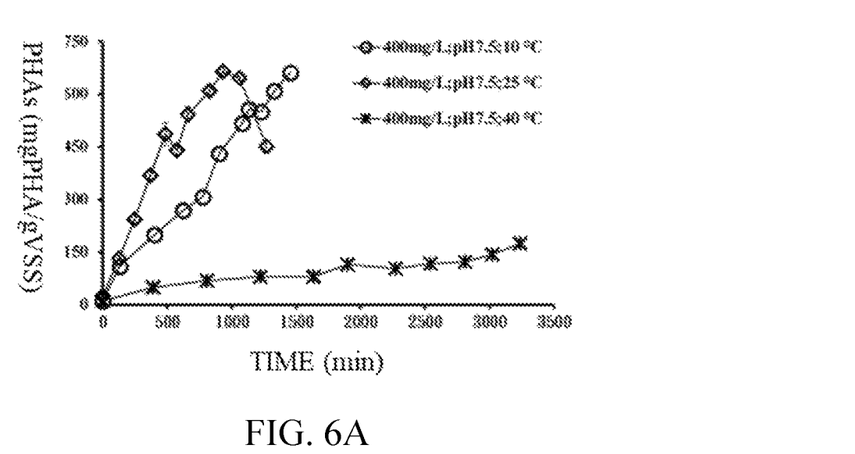
FIGS. 6A to 6C illustrate a best temperature and a best PH value for domesticating microorganism and best times for adding volatile fatty acid.
Figure 6B:
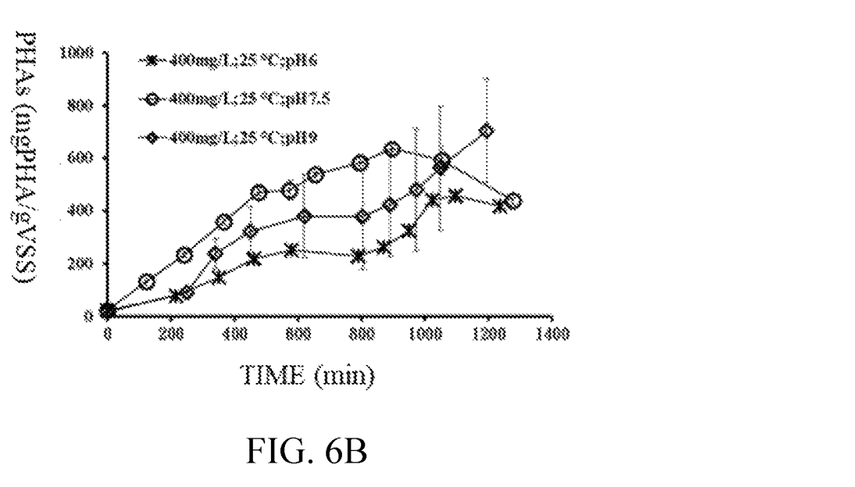
Figure 6C:
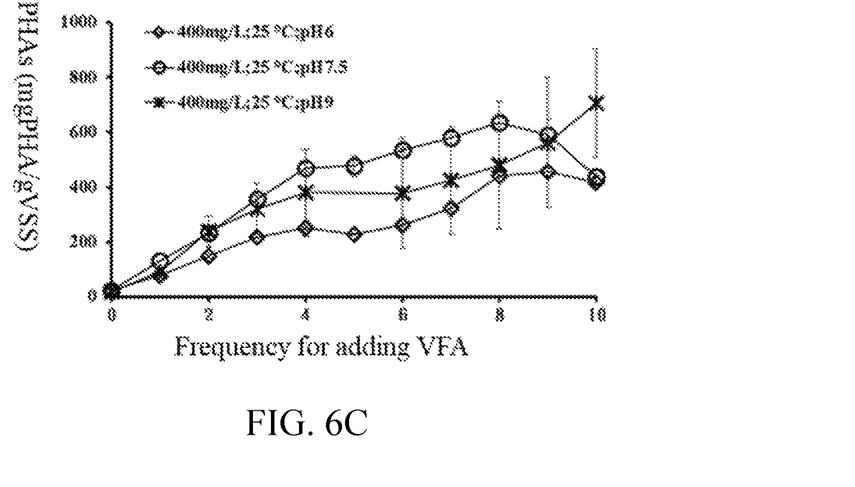

Embodiment 4 the Best Temperature, PH Value and Frequency for Adding VFA of ADF Domestication Microorganism Please refer to FIGS. 6A to 6C, which illustrates different temperatures and PH values influence the PHAs production when performing ADF domestication microorganism. The experiment uses different temperatures (10, 25, and 40° C., respectively) to perform ADF domestication, as shown in FIG. 6A, X axis is the time of ADF domestication, and Y axis is the production of PHAs (mg PHA/g VSS). As the result, when ADF domestication is performed and the temperature is 25° C., a very high PHAs production (665 mg PHA/g VSS) can be achieved in a short period (935 minutes). In addition, as shown in FIG. 6B, X axis is the time of ADF domestication, and Y axis is the production of PHAs (mg PHA/g VSS), from SPSS test, it can be found out that there is no apparent difference between the results of PH=7.5 and 9. Further, as shown in FIG. 6C, X axis is the frequency for adding VFA, and Y axis is the production of PHAs (mg PHA/g VSS). As the result, in the circumstance of PH values are 6, 7.5 and 9, respectively, the highest PHA production are 456 mg PHA/g VSS, 634 mg PHA/g VSS and 705 mg PHA/g VSS, respectively, that is, 45.6%, 63.4% and 70.5%. The VFA adding frequency corresponding to highest PHAs production are 9, 8 and 10 times. In conclusive, in a preferred embodiment of the present invention, ADF domestication microorganism is performed in a circumstance of PH=0.9 and adding 8~9 times VFA.

Figure 7:
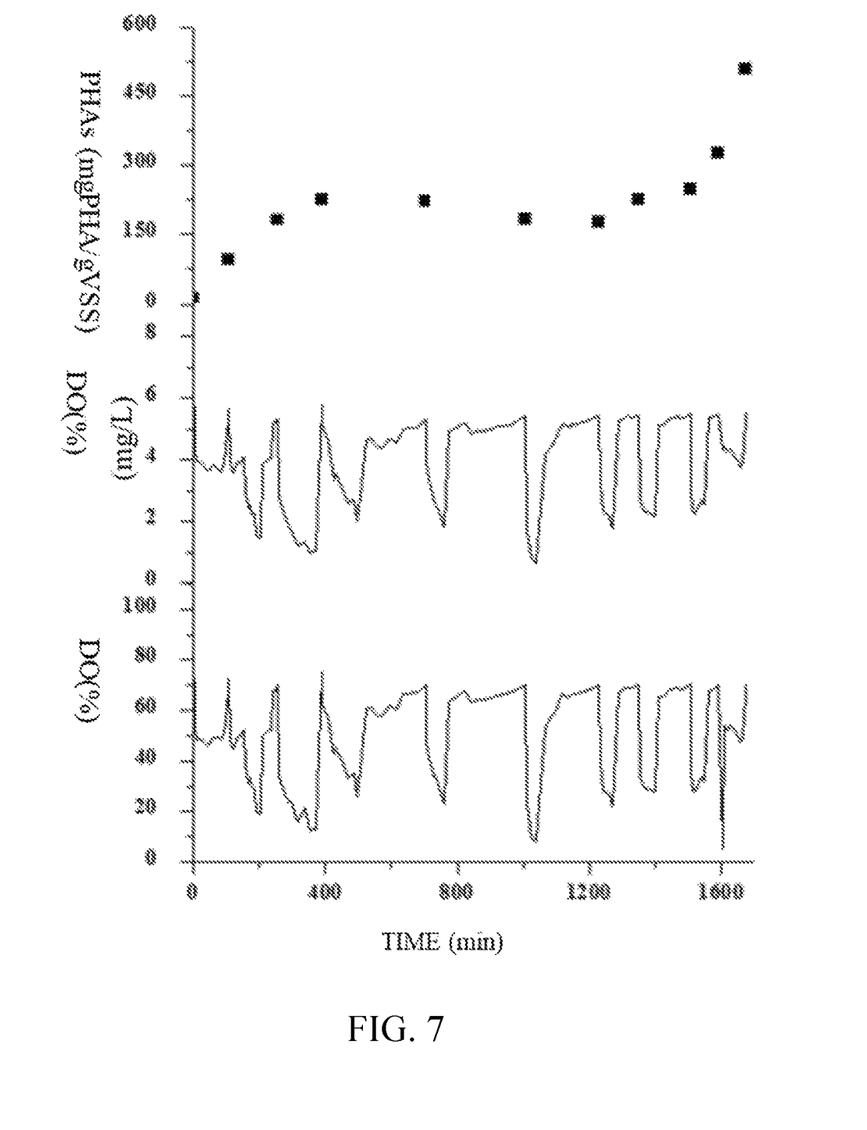
FIG. 7 illustrates the timing for adding volatile fatty acid when the ADF is domesticating microorganism.

Embodiment 5 the Timing for Adding VFA when Performing ADF Domestication Microorganism Please refer to FIG. 7, which illustrates adding 400 mg/L VFA and, controlling the temperature at 25° C. and using 5N $H_2SO_4$ and 5N NaOH to control the ph value to 9 to perform 10 times VFA adding experiments. After being aerated and activated, the DO of the waste sludge reaches 80% to perform domestication microorganism. As the result, in the first time VFA added to the waste sludge, that is, when the carbon source enters the tank, at the same time the DO drops because the microorganisms in the tank using the carbon source to consume Oxygen, and when the added carbon source is exhausted by the microorganisms, the DO rises to reach a balance. Therefore, in accordance with the DO variation trend of FIG. 7, in the duration of ADF domestication, when the added carbon source is exhausted, the corresponding balance DO is 70%, so in a preferred embodiment of the present invention, the DO in the tank right is timely monitored after every time adding VFA into the tank, and the timing for next time adding VFA is that when the DO reaches 70%.

A production comparison of the PHAs produced in accordance with the above embodiments and other synthesizing method can be shown as FIG. 8, wherein the PHAs of the present invention is in accordance with the parameters of above preferred embodiments, and is synthesized by the activated waste sludge and fermentation liquid of the above embodiments. As the result, by using the method of the present embodiments, 70% PHAs production can be made without complicated domestication steps and extra-added pharmacy, and the objects of lowering producing cost and raising productivity can be achieved at the same time.

According to the result of above embodiments, the present invention provides a method for increasing PHAs content of waste sludge, the method includes directly fermenting the waste sludge to achieve the fermentation liquid to be a carbon source, thereby lowering the raw material cost of microorganism domestication. In addition, by performing Oxygen aeration after diluting the waste sludge to raise the Oxygen content evenness of the activated waste sludge so as to raise the efficiency of following microorganism domestication. Furthermore, the aforesaid fermentation liquid is used for microorganism domestication, and the timing for adding an outside carbon source can be determined by timely monitoring the DO, therefore raising the efficiency of synthesizing microorganisms and accumulating PHAs. According to the method provided by the invention, the waste sludge can be effectively reused to achieve lowering the production cost and solving the accumulation problem of waste sludge. In another aspect, by using the method of the present invention, the complicated domestication process and long steps for monitoring carbon source are unnecessary, therefore reducing the complexity for producing PHAs and raising the producing efficiency thereof, and making PHAs having more industrial utilization.

What is claimed is:

1. A method for increasing polyhydroxyalkanoates (PHAs) content of waste sludge, comprising the steps of:
    diluting a first waste sludge with water and performing oxygen aeration and activation to get an activated waste sludge;
    fermenting a second waste sludge for 4 to 6 days at a temperature of 40-50° C. to get a fermentation liquid; wherein the fermentation liquid comprises volatile fatty acid selected from the group consisting of acetic acid (HAc), propanoic acid (HPr), isobutyric acid (iso-HBu), valeric acid (HVa), and any combination thereof; and
    injecting a portion of the fermentation liquid into the activated waste sludge when the Dissolved Oxygen (DO) level is 75-85%; subsequently injecting more of the fermentation liquid into the activated waste sludge when the Dissolved Oxygen (DO) level is 65-75%; and then repeating the injection step at the 75-85% DO level and at a 65-75% DO level each five to ten times.

2. The method for increasing PHAs content of waste sludge of claim 1, wherein before the step of diluting the waste sludge, the waste sludge is filtered to remove impurities and the pH value thereof is adjusted to 11.

3. The method for increasing PHAs content of waste sludge of claim 1, wherein in the step of diluting the waste sludge, the ratio of mixing the waste sludge and water is 1:1.

4. The method for increasing PHAs content of waste sludge of claim 1, wherein in the step of fermenting, the waste sludge is fermented with 40° C. for 5 days.

5. The method for increasing PHAs content of waste sludge of claim 1, wherein the fermentation liquid has a volatile fatty acid concentration of 300-500 mg/L.

6. The method for increasing PHAs content of waste sludge of claim 1, wherein the injecting step comprises injecting a portion of the fermentation liquid into the activated waste sludge when the dissolved oxygen level is 80% and subsequently injecting the fermentation liquid into the activated sludge when the dissolved oxygen (DO) level is 70%; and then repeating the injection step at the 80% DO level and at the 70% DO level each eight to ten times.

* * * * *